United States Patent [19]

Imai

[11] Patent Number: 5,793,833
[45] Date of Patent: Aug. 11, 1998

[54] METHOD OF AND APPARATUS FOR MEASURING AND ESTIMATING THE CLEANLINESS OF WAFER ACCOMMODATING MEMBERS

[75] Inventor: Toshihiko Imai, Fukushima, Japan

[73] Assignee: Shin-Etsu Handotai Co., Ltd., Tokyo, Japan

[21] Appl. No.: 665,809

[22] Filed: Jun. 19, 1996

[30] Foreign Application Priority Data

Jun. 22, 1995 [JP] Japan .................................. 7-179361
Jun. 22, 1995 [JP] Japan .................................. 7-179362

[51] Int. Cl.$^6$ ...................................... G06M 11/02
[52] U.S. Cl. ...................................... 377/10
[58] Field of Search ...................................... 377/10

[56] References Cited

U.S. PATENT DOCUMENTS

| | | | |
|---|---|---|---|
| 4,130,754 | 12/1978 | Fosslien | 377/12 |
| 5,100,476 | 3/1992 | Mase et al. | 134/1 |
| 5,585,729 | 12/1996 | Toshima et al. | 324/445 |

FOREIGN PATENT DOCUMENTS 5-109857   4/1993   Japan .

*Primary Examiner*—Margaret Rose Wambach
*Attorney, Agent, or Firm*—Evenson, McKeown, Edwards & Lenahan P.L.L.C.

[57] ABSTRACT

To evaluate cleanliness of wafer accommodating members used for storing or transporting of silicon, gallium arsenide or like semiconductor wafers, pure water is poured into a vessel-like wafer accommodating member, such as a wafer case body, a top cover, etc., capable of containing liquid therein, and then low frequency vibrations or supersonic wave is applied to the member. Alternatively, inner wafer accommodating members accommodated in the wafer case body, such as a wafer basket, a wafer retainer, etc., are accommodated in a vessel containing poured pure water, and the low frequency vibrations or supersonic wave is applied to the members. Then, the quantity of particles in the water is counted. Particles that have been attached to the wafer case or to inner wafer accommodating members accommodated therein, such as a wafer basket, a wafer retainer, etc., are made readily separable into the water, thus permitting quantitative detection of generation of particles from the inner wafer accommodating members.

24 Claims, 12 Drawing Sheets

5,793,833

METHOD OF AND APPARATUS FOR MEASURING AND ESTIMATING THE CLEANLINESS OF WAFER ACCOMMODATING MEMBERS

BACKGROUND OF THE INVENTION

1. Field of the Invention

This invention relates to a method of measuring and estimating the cleanliness of wafer accommodating members used for storing or transporting of silicon, gallium arsenide or like semiconductor wafers (hereinafter referred to simply as wafers), particularly a wafer accommodating member cleanliness determining method, which permits quantitative measurement and/or estimation of dust particles attached to wafer accommodating members and particles generated therefrom. The wafer accommodating member may be a wafer case comprising a wafer case body, a top cover and inner wafer accommodating members such as a wafer basket, a wafer retainer, etc. accommodated in the wafer case body or the top cover. This invention also to an apparatus used to carry out such method.

2. Description of the Related Art

FIG. 3 shows a wafer case 50 which is used for storing or transporting wafers. The wafer case 50 comprises a wafer basket 53 having a fin-like wafer accommodating section, in which a plurality of wafers 100 are accommodated in parallel, a wafer case body 1 for accommodating the wafer basket 53, a top cover 52 for closing the top opening of the wafer case body 1, a wafer retainer 54 for retaining the wafers 100 in the wafer basket 53 in position and the packing 55. The wafer case 50 is always required to be highly clean in order to minimize particles attached to the surfaces of the accommodated wafers 100 while the wafers are stored or transported.

The wafer case 50 is usually formed by injection molding a thermoplastic resin, such as polypropylene, polycarbonate, etc., into a desired shape. Therefore, dust particles are attached to the surfaces of the molded wafer case 50. Such particles have to be removed by measuring and estimating the cleanliness of the wafer case 50 after the molding thereof. Particle removal is done in this way before using the wafer case for storing or transporting the wafers 100.

Such cleanliness estimation, particularly the detection of the particle attachment status, has hitherto been done by the following methods.

(1) Particles remaining on inner surfaces of the wafer case after cleaning thereof are visually detected.

(2) Particles present in rinsing water, in which the wafer case has been cleaned, are determined by counting.

(3) As shown in Japanese Laid-Open Patent Publication No. Heisei 5-1098578, the wafers are rotated in clean air atmosphere by a wafer rotating device from the bottom of the wafer basket for a predetermined period of time, and the particles generated as a result of friction between wafer holding grooves formed in inner surfaces of the wafer basket and the edge of wafers is measured by a dust measuring instrument. When a predetermined threshold particle count is exceeded, it is determined that the cleanliness is insufficient.

The above wafer case cleanliness determination methods, however, have the following problems or drawbacks.

(1) The visual method shown in (1) above is applicable only to detect relatively large size particles. Therefore, the method cannot meet the recent demand for the ability of detecting finer particles accompanying a finer, recent semiconductor integrated circuit structure trend. Besides, the method is based on visual operation alone and therefore lacks quantitative property.

(2) In the method shown in (2) above, particles in rinsing fluid or water after cleaning of the wafer case are counted. This means that particles which remain without being separated into the rinsing fluid or water during cleaning, cannot be quantitatively detected. In addition, particles that are generated from the wafer case itself cannot be detected.

(3) The method shown in (3) above is free from the drawbacks in the methods in (1) and (2). This method, however, requires many accessory devices such as a wafer rotating mechanism and accessories therefor. This leads to complicated structure and high cost of the evaluation equipment.

SUMMARY OF THE INVENTION

Objects of the Invention

An object of the invention is to provide a method of quantitatively detecting and estimating particles attached to and also generated from wafer accommodating members used for storing or transporting semiconductor wafers with an apparatus which is relatively simple in structure and can be provided at a low cost.

Another object of the invention is, in view of recent demands for re-using, instead of discarding, wafer accommodating members made of resins for resources protection and also for coping with environment contamination, to provide a method of estimating the cleaning degree of a wafer accommodating members after cleaning in order to re-use wafer accommodating members.

Constitution

One feature of the invention resides in a method of measuring and estimating the cleanliness of wafer accommodating members used for storing and transporting semiconductor wafers comprising the steps of:

accommodating wafer accommodating members in a vessel with a bottom and then pouring a predetermined amount of pure water into the vessel, or pouring a predetermined amount of pure water directly into a wafer accommodating member in the form of a vessel with a bottom;

putting the vessel or the wafer accommodating member in the form of a vessel with a bottom after the pouring of pure water on a vibrator and counting the particles in the water after the stabilization of the water level and before application of vibrations;

then applying low frequency vibrations to the vessel and wafer accommodating members therein or to the wafer accommodating member in the form of a vessel with a bottom from the vibrator for a predetermined period of time; and counting the particles in the water again to obtain the increase of particle count after the application of vibrations and estimating the cleanliness of the wafer accommodating member from the increase of the particle count thus obtained.

Suitably, the low frequency vibrations that are applied are sinusoidal vibrations or like regularly recurring vibrations. Suitably, the frequency of the low frequency vibrations is set to 50 to 2,000 Hz. Suitably, the acceleration of the low frequency vibrations is set to 2 to 50 G. Suitably, the low frequency vibrations are applied in vertical directions.

In a wafer case which comprises a wafer basket for accommodating semiconductor wafers, a wafer retainer for the wafer basket, a wafer case body for accommodating the wafer basket and the wafer retainer, and a top cover for closing the wafer case body, the wafer basket, the wafer retainer, etc. accommodated in the wafer case, are accommodated as under-measurement members in the vessel with a bottom before pouring the predetermined amount of pure water into the vessel. An under-measurement member is defined as a member whose cleanliness is being measured by the present invention.

In a wafer case which comprises a wafer basket for accommodating wafers, a wafer retainer for the wafer basket, a wafer case body for accommodating the wafer basket and the wafer retainer, and a top cover for closing the wafer case body, suitably the wafer case body or the top cover is put as an under-measurement member in the form of a vessel on the vibrator before pouring pure water into it.

According to the invention, it is possible to use supersonic wave vibrations instead of the low frequency vibrations.

That is, another feature of the invention resides in:
accommodating wafer accommodating members used for storing or transportation of semiconductor wafers in a vessel with a bottom and then pouring a predetermined amount of pure water into the vessel, or pouring a predetermined amount of pure water directly into a wafer accommodating member in the form of a vessel with a bottom;

putting, after the pouring of pure water, the vessel with the wafer accommodating members therein or the wafer accommodating member in the form of a vessel with a bottom in a water trough provided with a supersonic wave generator;

counting the particles in the water after the stabilization of the water level and before the application of the supersonic wave;

then applying supersonic wave vibrations to the vessel and the wafer accommodating members therein or to the wafer accommodating member in the form of a vessel with a bottom from the supersonic wave generator for a predetermined period of time;

counting, after the application of the supersonic wave, the particles in the water again to obtain the increase of particle count; and estimating the cleanliness of the wafer accommodating member from the increase of particle count thus obtained.

Suitably, the frequency of the supersonic wave vibrations is set to 20 to 50 kHz. Also, suitably the supersonic wave output is set to 300 to 400 W.

In the case where the wafer accommodating members are inner wafer accommodating members such as the wafer basket, the wafer retainer, etc., accommodated in the wafer case, these wafer accommodating members are accommodated in a vessel with a bottom before pouring the predetermined amount of pure water into the vessel.

Suitably, the supersonic wave vibrations are attenuated between the supersonic wave generator and the inner wafer accommodating members which are dipped in the water in the vessel by a supersonic wave attenuating means, so that the attenuated supersonic wave vibrations are applied to the inner wafer accommodating members. Suitably, the pure water is poured into the vessel until it reaches a level 5 mm above to 40 mm below the top of the wafer accommodating members.

In the case where a wafer accommodating member is the wafer case body or the top cover, suitably the wafer case or the top cover is disposed as an under-measurement member in the form of a vessel, after pouring pure water into it, in a water trough provided with a supersonic wave generator.

Again in this case, suitably the supersonic wave vibrations are attenuated between the supersonic wave generator and the under-measurement member, i.e., the wafer case body or the top cover by a supersonic wave attenuating means, so that the attenuated supersonic wave is applied to the under-measurement member. Suitably, the pure water is poured in an amount corresponding to 35 to 95% of the inner volume of the under-measurement member.

The invention further features the following wafer accommodating member cleanliness measuring and estimating apparatuses.

One such apparatus according to the invention is for measuring and estimating the cleanliness of inner wafer accommodating members accommodated in the wafer case, such as the wafer basket, the wafer retainer, etc., by using low frequency vibrations, and comprises:

a vessel with a bottom which pure water is poured into, the inner wafer accommodating members being dipped in the poured pure water;

a vibrator for vibrating the vessel; and a particle measuring apparatus coupled to the water in the vessel for measuring the particle count in the water.

Another apparatus according to the invention is for measuring and estimating the cleanliness of inner wafer accommodating members accommodated in the wafer case, such as the wafer basket, the wafer retainer, etc., by using a supersonic wave, and comprises:

a vessel with a bottom which pure water is poured into, the inner wafer accommodating members being dipped in the poured pure water;

a water trough for accommodating the vessel with outer wall surfaces thereof dipped in the water;

a supersonic wave generator disposed underneath the vessel in the water trough for applying supersonic wave vibrations to the inner wafer accommodating member in the vessel; and a particle measuring apparatus coupled to the water in the vessel for measuring the particle count in the water.

In this case, suitably a supersonic wave attenuating means for attenuating the supersonic wave is provided between the supersonic wave generating apparatus and the vessel.

A further apparatus according to the invention is for measuring and estimating the cleanliness of a wafer accommodating members including a wafer basket body for accommodating a wafer basket for accommodating wafers and a top cover for the wafer case body by using low frequency vibrations, and comprises:

a vibrator for vibrating the wafer case body or the top cover as an under-measurement member in the form of a vessel under a condition that the under-measurement member contains a predetermined amount of poured pure water; and a particle measuring apparatus coupled to the water in the under-measurement member for measuring the particle count in the water.

A still further apparatus according to the invention is for measuring and estimating the cleanliness of a wafer accommodating members including a wafer case body for accommodating a wafer basket for accommodating wafers and a top cover for the wafer case body by using a supersonic wave, and comprises:

an under-measurement member in the form of a vessel constituted by the wafer case body or the top cover and containing poured pure water;

a water trough accommodating the under-measurement member such that outer wall surfaces thereof are dipped in the water;

a supersonic wave generator disposed underneath the under-measurement member in the water trough for applying a supersonic wave to the under-measurement member; and a particle measuring means coupled to the water in the under-measurement member for measuring the particle count in the water.

Again in this case, suitably a supersonic wave attenuating means for attenuating the supersonic wave is provided between the supersonic wave generator and the under-measurement member.

Suitably, the particle measuring apparatus according to the invention is capable of measuring particles in water and with sizes up to about 0.1 μm.

Suitably, the supersonic wave attenuating means is in the form of a vessel with a bottom which accommodates the vessel with a bottom accommodating the inner wafer accommodating member, and is made of polypropyrene, polyethylene or polycarbonate, suitably for which it uses both as the vessel with bottom and the supersonic wave attenuating means.

In the case where the wafer case body which accommodates the wafer basket for accommodating wafers and the top cover are under-measurement members, the supersonic wave attenuating means is in the form of a vessel capable of accommodating the under-measurement members and is made of polypropyrene, polyethylene or polycarbonate.

Effects of the Invention

According to the invention utilizing the low frequency vibrations, since the low frequency vibrations are applied to the vessel putting on the vibrator and also to the inner wafer accommodating members accommodated in the vessel in the state of being dipped in pure water, particles that have been attached to the inner wafer accommodating members can be made readily separable into the water. In addition, it is possible to detect particles generated from the inner wafer accommodating members themselves. During transportation of wafers, the wafer accommodating members accommodating the wafers are subject to vibrations. For this reason, it is necessary to accurately grasp not only the particles separated from inner wall surfaces of the wafer accommodating members but also the particles generated from the wafer accommodating members themselves. This requirement can be sufficiently met by the above arrangement according to the invention.

Besides, since the pure water poured into the vessel accommodating the inner wafer accommodating members is coupled via a tube to the particle measuring apparatus for progressive measurement of the particles, it is possible to grasp changes in the generated particles with the lapse of time.

It is further possible to measure and estimate the cleanliness of inner wafer accommodating members, which are not vessel-like and incapable of pouring pure water into them, such as the wafer basket or the wafer retainer, by dipping the inner wafer accommodating members in pure water poured into a vessel which can accommodate the inner wafer accommodating members.

It is furthermore possible to obtain satisfactory reproducibility of vibrations applied to the inner wafer accommodating member in the wafer case by applying low frequency vibrations of a sinusoidal wave less subject to frequency and acceleration fluctuations under adequate frequency and acceleration conditions. This permits more quantitative determination of the cleanliness of the inner wafer accommodating members in the wafer case through comparison of the particle count in water before and after the application of the low frequency vibrations for a predetermined period of time.

By applying the low frequency vibrations vertically, it is possible to prevent leakage of the water from above the vibrator.

This is so as well in the case where the low frequency vibrations are applied to the wafer case body containing pure water poured thereinto or the top cover (i.e., the under-measurement member) which is put on the vibrator.

According to the invention utilizing the supersonic wave, since the supersonic wave is applied to the vessel, the wafer case therein or the inner wafer accommodating members in the wafer case, the inner wafer accommodating members being accommodated in the state of being dipped in pure water in the wafer case which is in turn accommodated in the state of being dipped in pure water in the vessel, the vessel being on a vibrating table, particles that have been attached to the surfaces of the inner wafer accommodating members and the wafer case can be made readily separable into the water. In addition, it is possible to detect particles generated from the inner wafer accommodating members and wafer case. The same effects as in the case utilizing the low frequency vibrations are thus obtainable.

It is further possible to obtain satisfactory reproducibility of vibrations applied to the wafer case and the inner wafer accommodating member by applying a supersonic wave which is less subject to frequency and output fluctuations. More quantitative determination of the cleanliness of the wafer case is thus obtainable through comparison of the particle count in water before and after the application of the supersonic wave vibrations for a predetermined period of time.

It is furthermore possible to reduce the frequency and output fluctuations and obtain enhanced effects of application of vibrations by setting the supersonic wave in the frequency and output ranges as noted above.

Moreover, when the supersonic wave output becomes excessive, it may be attenuated with the supersonic wave attenuating means before it is applied to the under-measurement members.

Yet further effects of the invention are obtainable by pouring the pure water into the vessel to reach a water level 5 mm above or 40 mm below the top of the wafer accommodating members or pouring the pure water into the under-measurement members in an amount corresponding to 35 to 95% of the inner volume of the under-measurement members. That is, doing so permits measurement of particles without sacrifice in the accuracy even with a wafer basket, the density of which after the molding is lower than unity. In other words, by setting the amount of pure water poured into the wafer case to be in the above ranges, the cleanliness measurement is possible with an amount of pure water permitting ready intrusion of particles from the inner wafer accommodating members in the wafer case, thus permitting improvement of the accuracy of measurement.

DETAILED DESCRIPTION OF THE PREFERRED EMBODIMENTS

Preferred embodiments of the invention will now be described in detail with reference to the drawings. It is to be construed that unless particularly noted, the sizes, materials, shapes, relative dispositions, etc. of constituent parts described in the embodiments have no sense of limiting the scope of the invention but are mere examples.

(A) First Embodiment

Figure 1:
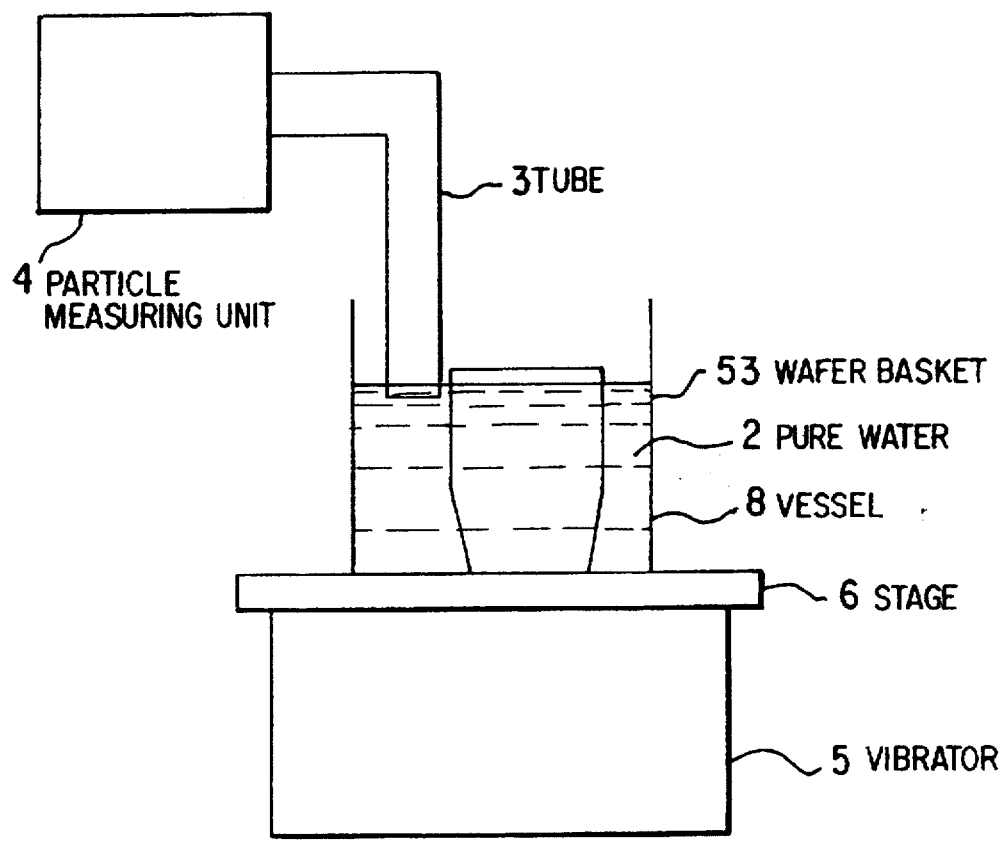
FIG. 1 is a schematic view showing an apparatus for measuring and estimating the cleanliness of inner wafer accommodating members of a wafer case (by applying low frequency vibrations) according to a first embodiment of the invention.

FIG. 1 schematically shows an apparatus for estimating the cleanliness of a wafer basket according to a first embodiment of the invention.

Referring to FIG. 1, reference numeral 53 designates a wafer basket which is accommodated in a vessel 8 with a bottom. The vessel 8 accommodating the wafer basket 53 is put on a stage 6 which is provided on a vibrator 5. Vibrating forces are thus applicable from the vibrator 5 to the vessel 8 accommodating the wafer basket 53 via the stage 6.

The vessel 8 is made from a stainless steel sheet and coated with a fluorocarbon resin, but it may be made of quartz, glass, aluminum, plastic materials, etc. as well.

The vessel 8 contains pure water 2 in an amount corresponding to about 80% (preferably 60 to 95%) of its inner volume. A particle measuring unit 4 for measuring the particle count in the water 2 in the vessel 8, is communicated with the water 2 in the vessel 8 through a tube 3. The particle count in the water 2 thus can be measured progressively.

A method of measuring and estimating the cleanliness of inner wafer accommodating members of the wafer case shown in FIG. 1 will now be described.

Test Example 1

(1) The vessel 8 was filled with pure water 2 and then treated in a supersonic wave trough, and then the water was discharged. Then, the wafer basket 53 was accommodated in the vessel 8, and pure water 2 was poured again until its level reaches about 1 cm below the top of the wafer basket 53.

After the level of the water 2 had been stabilized, the particles having sizes of 0.2 μm and above in the water were counted with the particle measuring unit 4.

(2) Subsequently, sinusoidal wave Low frequency vibrations at a frequency of 1,000 Hz and with an acceleration of 15 G, were applied to the vessel 8, the wafer basket 53 and the water 2 from the vibrator 5 via the stage 6. The vibrations were applied continuously for 30 minutes while counting the particles in the water with the particle measuring unit 4 for every one minute.

Figure 4:
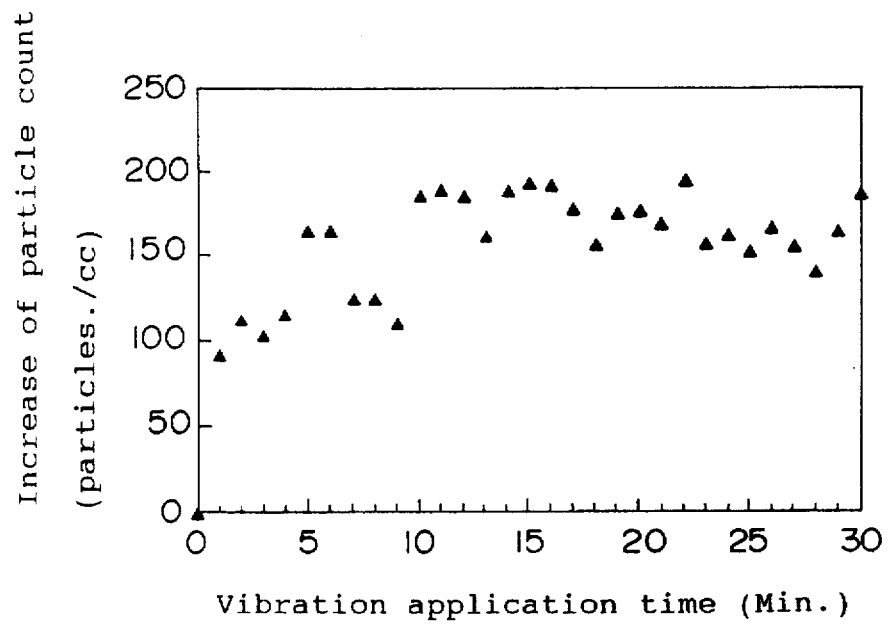
FIG. 4 is a graph showing test results in the first embodiment of the invention.

(3) FIG. 4 shows the results of the test conducted in (1) through (2) above.

As is obvious from FIG. 4, the particle count in the water was substantially saturated after about 10 minutes. That is, after about 10 minutes of vibration application, the particles that had been attached to the wafer basket 53 were separated into the water 2, so that the wafer basket 53 was purified.

Test Example 2

(1) The same operation and measurement as in (1) in Test Example 1 were done.

(2) Sinusoidal wave low frequency vibrations at a frequency of 1,000 Hz and with an acceleration of 15 G, were continuously applied for 20 minutes from the vibrator 5.

(3) Then, the water 2 in the vessel 8 was discharged, and the same amount of pure water as the discharged amount was poured into the vessel 8, and the particles in the water 2 were counted with the particle measuring unit 4 after the water level stabilization.

(4) Then, the same low frequency vibrations as in (2) were applied for 10 minutes while counting the number of particles in the water for every one minute with the particle measuring unit 4.

Figure 5:
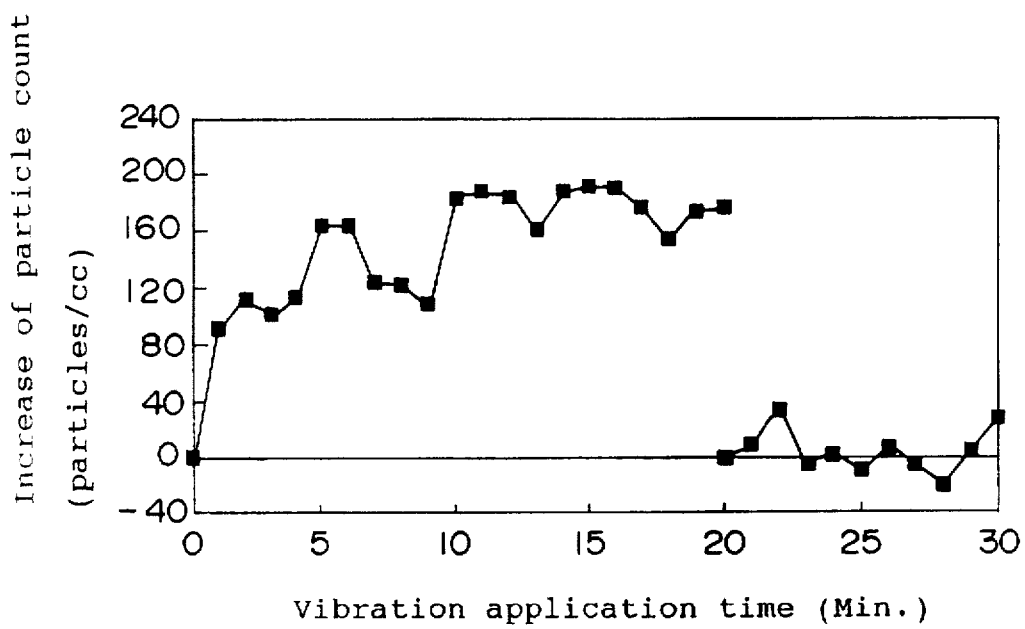
FIG. 5 is a graph showing test results in the second embodiment of the invention.

(5) FIG. 5 shows the results of the test conducted in (1) through (4) above.

As is obvious from FIG. 5, after the initially poured water 2 had been discharged from the vessel 8, substantially no particle was detected by pouring pure water again and applying vibrations. This indicates that application of the low frequency vibrations to the pure water in the vessel 8 accommodating the wafer basket 53 causes efficient separation of particles from the wafer basket 53.

Test Example 3

(1) Ten wafer baskets 53 right after the molding and also ten wafer baskets 53 after cleaning were prepared.

(2) Each wafer basket 53 was accommodated in the vessel 8, then pure water 2 was poured thereinto. Then, as in Test Example 1, sinusoidal wave low frequency vibrations at a frequency of 1,000 Hz and with an acceleration of 15 G were applied for 10 minutes, and then the particles in the water were counted.

Figure 6:
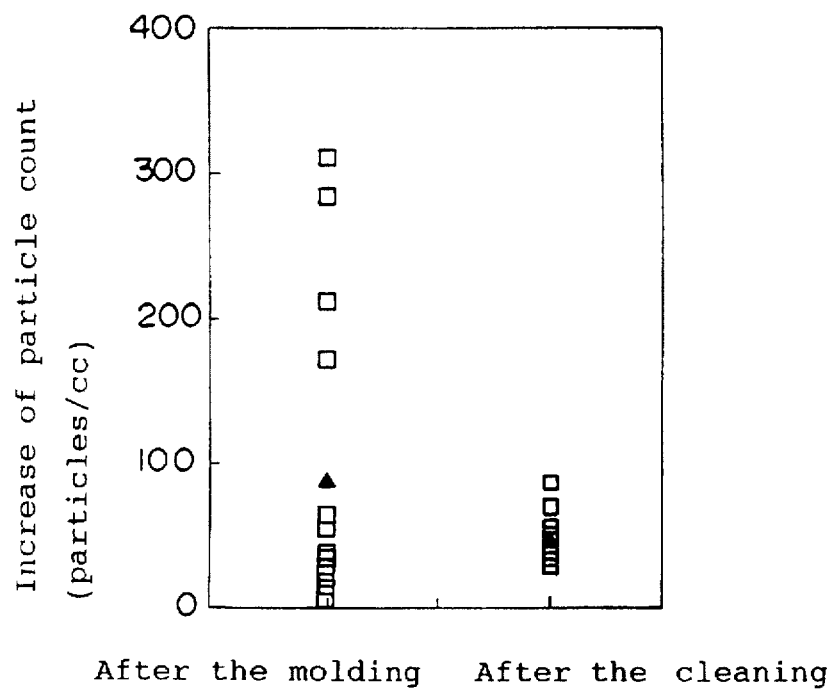
FIG. 6 is a graph showing test results in the third embodiment of the invention.

(3) FIG. 6 shows the results of the test conducted in (1) through (2) above.

As is obvious from FIG. 6, the particle count in the water was greatly less with the wafer baskets after the cleaning than with those right after the molding (i.e., without being washed), indicating cleanliness increase of the wafer basket 53 by cleaning.

Test Example 4

(1) The wafer retainer 54 (see FIG. 3) was dipped in pure water 2 contained in the vessel 8, and after stabilization of the water level the particles having sizes of 0.2 μm and above in the water were counted.

(2) Then, sinusoidal wave low frequency vibrations at a frequency of 1,000 Hz and with an acceleration of 20 G from the vibrator 5, were applied for 20 minutes while measuring the particle count in the water at an interval of one minute.

(3) Then, the water in the vessel 8 was discharged, and the same amount of pure water as the discharged amount was poured again into the vessel 8. After the water level stabilization, the particles in the water were counted again.

(4) Then, the same sinusoidal wave low frequency vibrations as in (2) above were applied for 10 minutes while measuring the particle count in the water at an interval of one minute.

Figure 7:
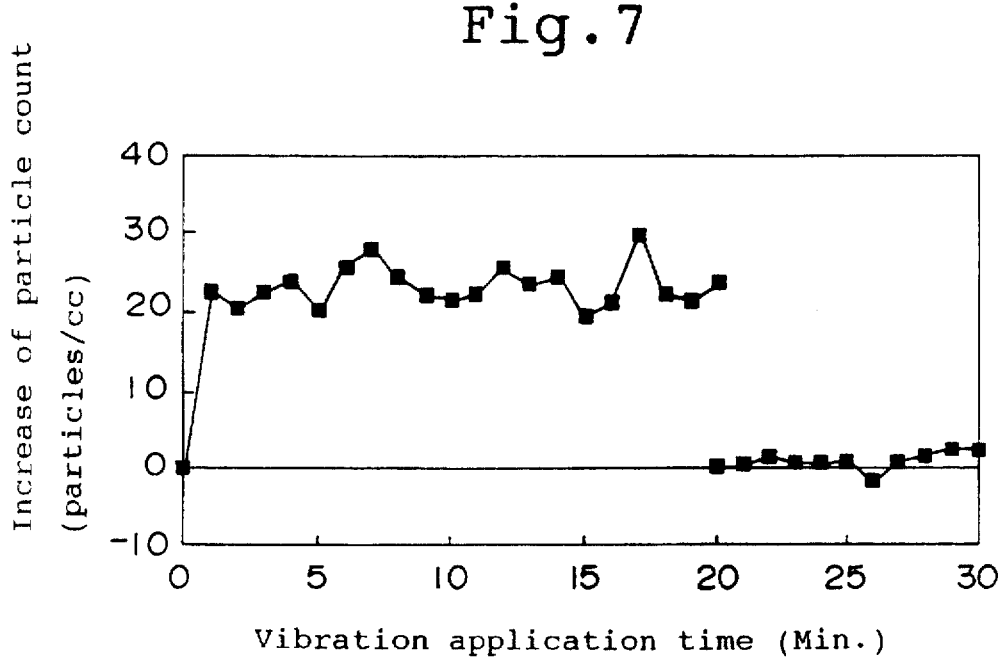
FIG. 7 is a graph showing test results in the fourth embodiment of the invention.

(5) FIG. 7 shows the result of measurement by the above measurement method.

As is obvious from FIG. 7, after the initially poured pure water had been discharged from the vessel 8, substantially no particle was detected by pouring pure water again, indicating that application of the low frequency vibrations to the water with the wafer retainer 54 dipped therein causes efficient separation of particles from the wafer retainer.

(B) Second Embodiment

Figure 2:
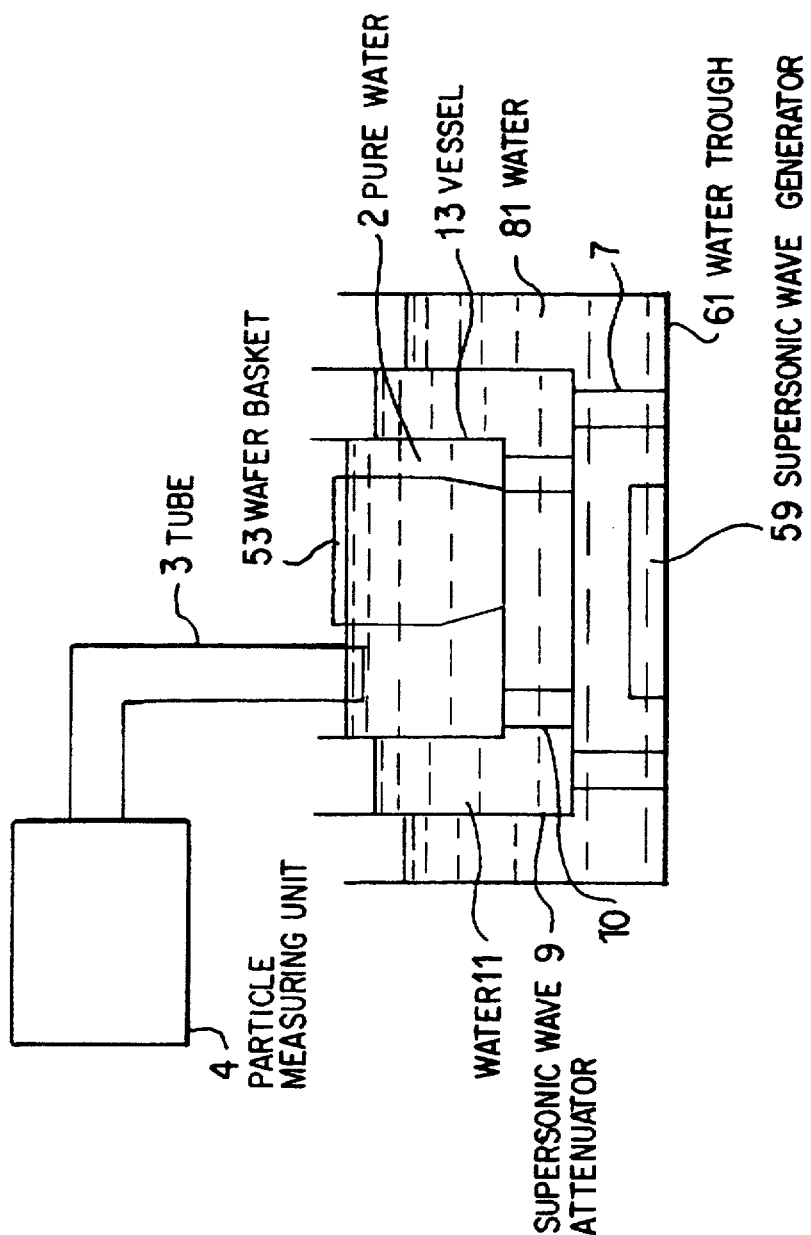
FIG. 2 is a schematic view showing an apparatus for measuring and estimating the cleanliness of inner wafer accommodating members of a wafer case (by applying supersonic wave vibrations) according to a second embodiment of the invention.

FIG. 2 schematically shows an apparatus for measuring and estimating the cleanliness of a wafer basket as an inner wafer accommodating member in a wafer case according to a second embodiment of the invention.

Figure 3:
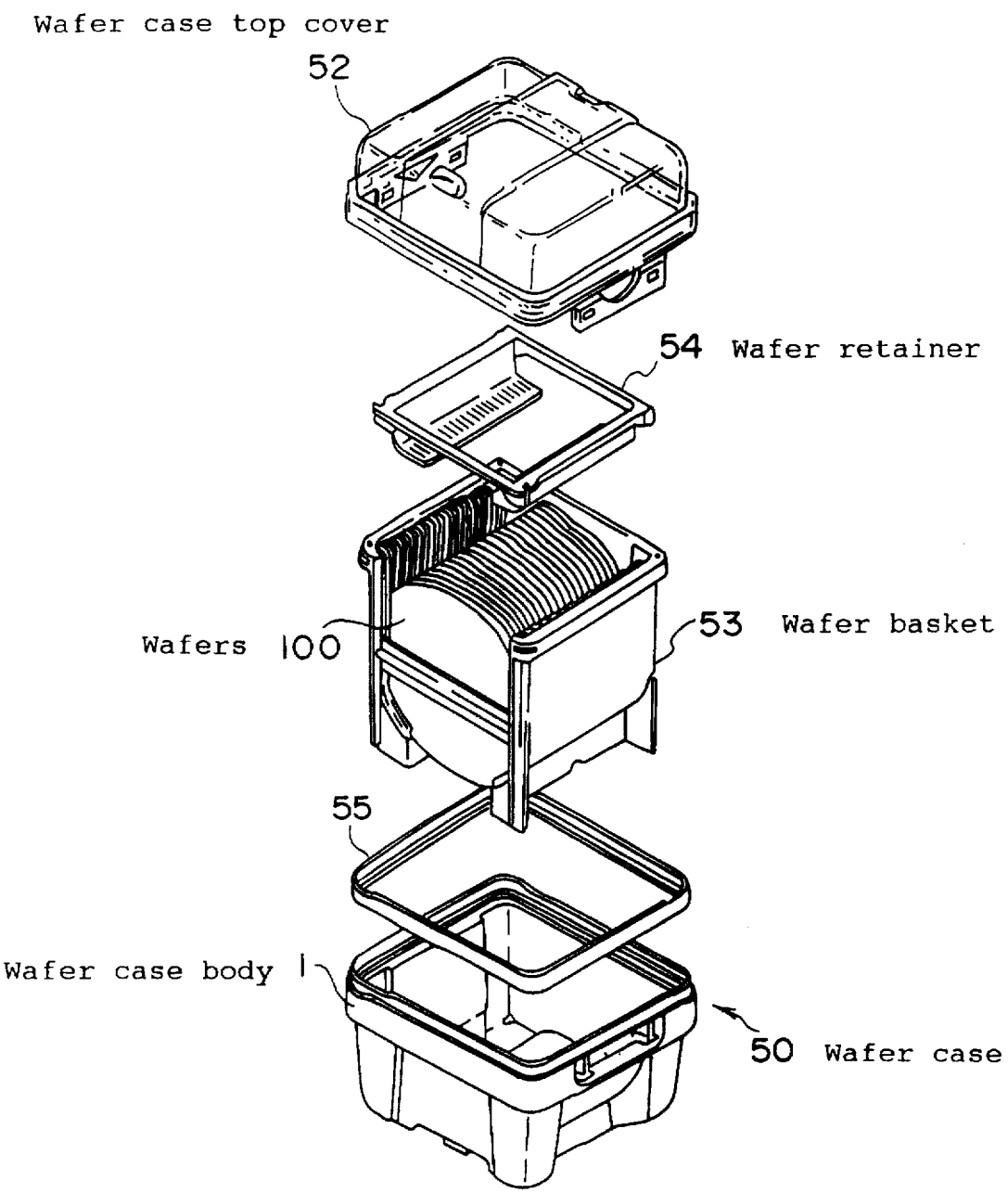
FIG. 3 is an exploded perspective view showing the wafer case (i.e., wafer accommodating member)

Referring to FIG. 2, reference numeral 53 designates the wafer basket shown in FIG. 3, which is dipped in pure water 2 contained in a vessel 13 with a bottom.

The pure water 2 is contained in an amount that its level is 5 mm above to 40 mm below the top of the wafer basket 53. The measurement of the particle count is thus made possible even when the density of the wafer basket 53 after the molding is below unity (1).

Reference numeral 61 designates a water trough containing water 81. A supersonic wave generator 59 is installed on the bottom of the water trough 61.

Reference numeral 9 designates a supersonic wave generator for attenuating the supersonic wave from the supersonic wave generator 59 down to an intensity adequate for application to the wafer basket 53. Water 11 is contained in the attenuator 9.

The attenuator 9 is made of such material as polypropyrene, polyethylene, polycarbonate, etc.

The supersonic wave attenuator 9 is supported above the water trough 61 by a plurality of support legs 7, and the vessel 13 is supported by a plurality of support legs 10 erected upright from the bottom of the supersonic wave attenuator 9.

A particle measuring unit 4 for measuring the particle count in the vessel 13, is communicated with pure water 2 in the vessel 13 through a tube 3 for progressive measurement of particles in the water 2.

A method of measuring and estimating the cleanliness of inner wafer accommodating members (i.e., the wafer basket 53 and the wafer retainer 54) in the wafer case shown in FIG. 2 will now be described.

Test Example 5

(1) The wafer basket 53 was dipped in pure water 2 contained in the vessel 13, and after stabilization of the level of water 2 the particles having sizes of 0.2 µm and above in the water were counted.

(2) Then, supersonic wave vibrations at a frequency of 40 kHz and with an output of 300 W were applied from the supersonic wave generator 59 for 20 minutes while measuring the particle count at an interval of one minute.

(3) Then, the water in the vessel 13 was discharged, and the same amount of pure water as the discharged amount was poured into the vessel 13, and after the water level stabilization the particles in the water were counted.

(4) Then, the same supersonic wave as in (2) above was applied for 10 minutes while measuring the particle count at an interval of one minute.

Figure 8:
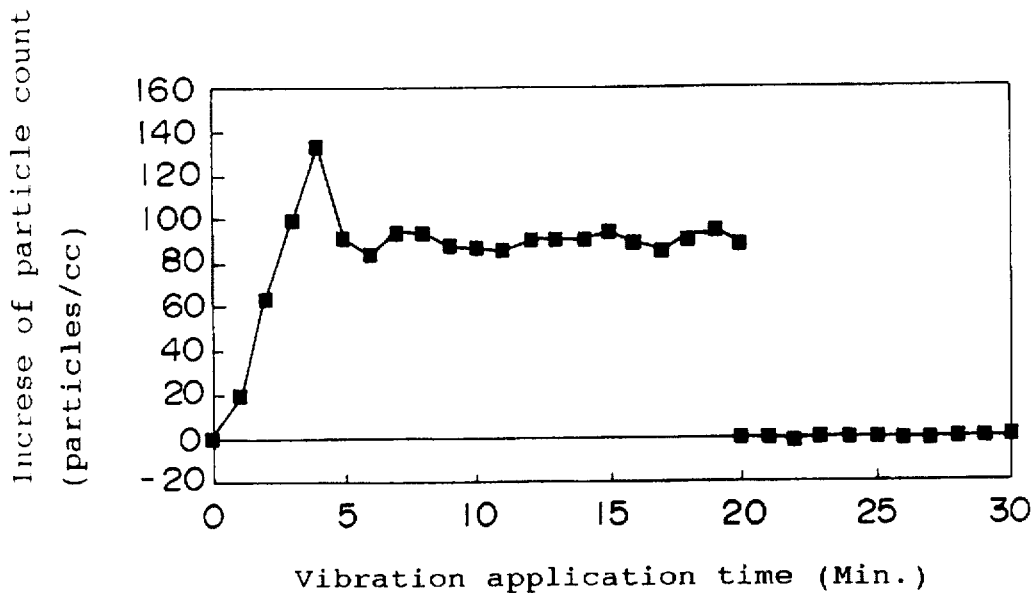
FIG. 8 is a graph showing test results in the fifth embodiment of the invention.

(5) FIG. 8 shows the result of measurement by the above method of measurement.

As is obvious from FIG. 8, after the initially poured water had been discharged from the vessel 13 substantially no particle was detected by pouring pure water again, thus indicating that the application of the supersonic wave to the water with the wafer basket dipped therein causes effective separation of particles from the wafer basket.

Test Example 6

(1) The wafer retainer 54 (see FIG. 3) was dipped in pure water 2 contained in the vessel 13, and after the stabilization of the level of water 2 the particles having sizes of 0.2 µm and above in the water were counted.

(2) Then, supersonic wave vibrations at a frequency of 40 kHz and with an output of 300 W, were applied from the supersonic wave generator 59 for 20 minutes while measuring the particle count at an interval of one minute.

(3) Then, the water in the vessel 13 was discharged, and the same amount of pure water as the discharged amount was poured again into the vessel 13, and after the water level stabilization the particles in the water were counted.

(4) Then, the same supersonic wave vibrations as in (2) above were applied for 10 minute while measuring the particle count at an interval of one minute.

Figure 9:
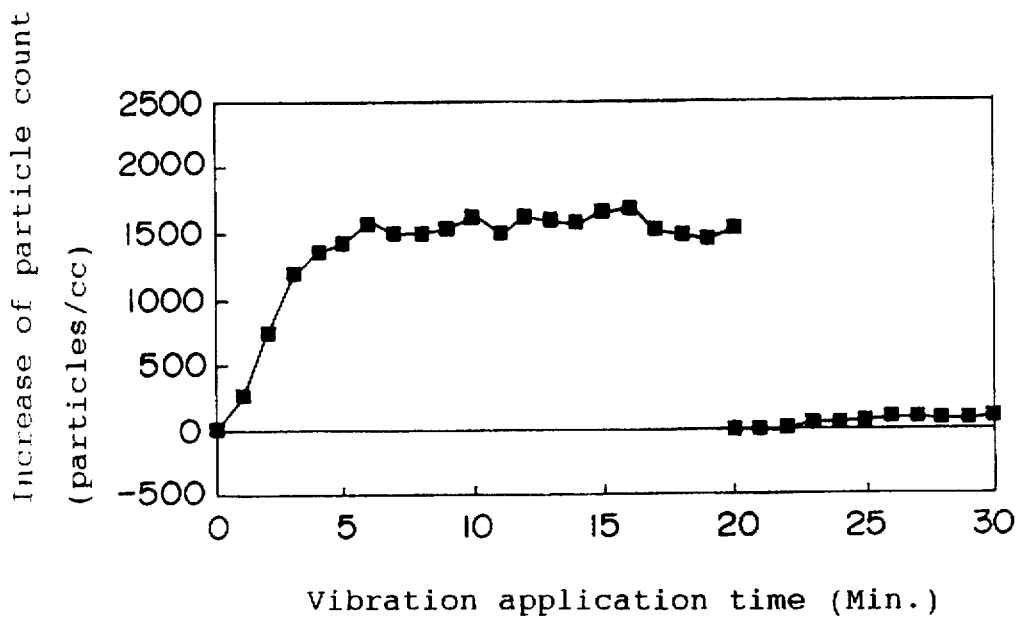
FIG. 9 is a graph showing test results in the sixth embodiment of the invention.

(5) FIG. 9 shows the result of measurement by the above method of measurement.

As is obvious from FIG. 9, after the initially poured water had been discharged from the vessel 13, substantially no particle was detected by pouring pure water again, indicating that the application of the supersonic wave to the water with the wafer retainer 54 dipped therein causes efficient separation of particles from the wafer retainer.

(C) Third Embodiment

Figure 10:
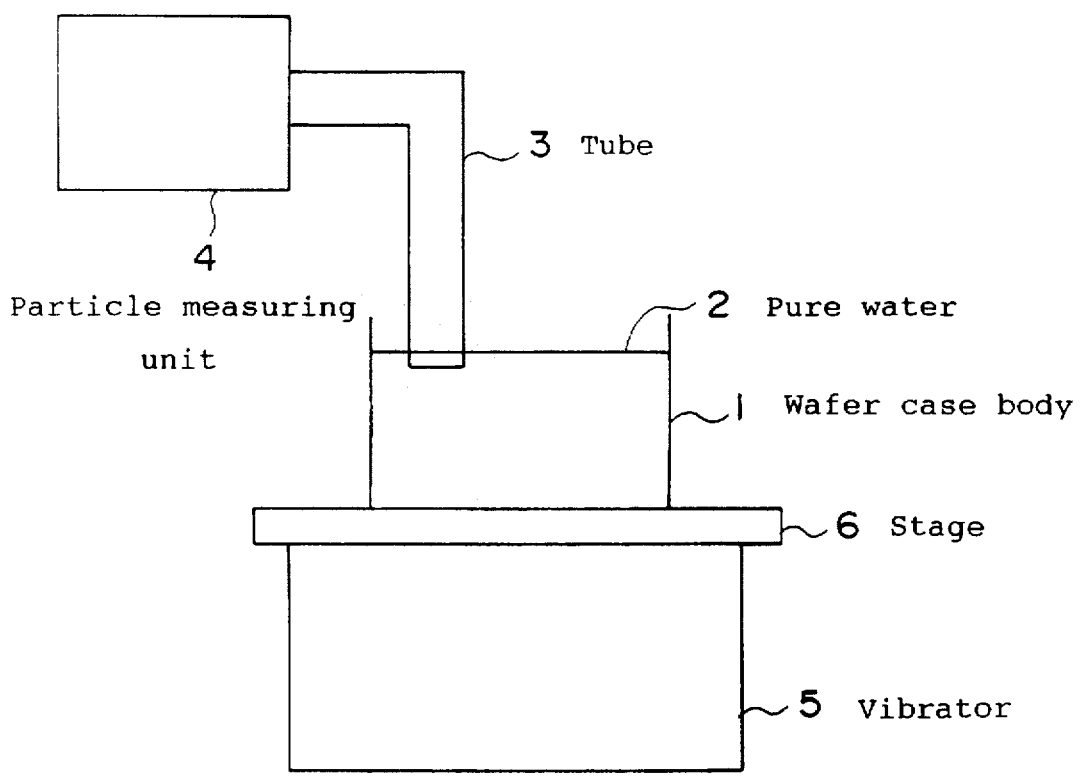
FIG. 10 is a schematic view showing an apparatus for measuring and estimating the cleanliness of a wafer case (by application of low frequency vibrations) according to the third embodiment of the invention.

FIG. 10 schematically shows an apparatus for estimating the cleanliness of a wafer case body according to a third embodiment of the invention. Referring to FIG. 10, reference numeral 1 designates the wafer case body shown in FIG. 3. The wafer case body 1 is put on a stage 6 which is coupled to a vibrator 5 for applying sinusoidal wave vibrations to it via the stage 6.

The wafer case body 1 contains pure water 2 poured to an amount corresponding to about 80% (preferably 35 to 95%) of its inner volume. A particle measuring unit 4 for measuring the particle count in the water 2, is communicated with the water 2 in the wafer case body 1 through a tube 3. The particle count in the water 2 thus can be measured progressively.

A method of measuring and estimating the cleanliness of the wafer case with the apparatus shown in FIG. 10 will now be described.

Test Example 7

(1) Pure water 2 was poured into the wafer base body 1, and after stabilization of the level of water 2 the particles having sizes of 0.2 µm and above in the water were counted with the particle measuring unit 4.

(2) Then, sinusoidal wave low frequency vibrations at a frequency of 900 Hz and with an acceleration of 20 G, were applied from the vibrator 5 to the wafer case body 1 and the water 2 therein. The low frequency vibrations were applied for 30 minutes while measuring the particle count in the water 2 at an interval of one minute with the particle measuring unit 4.

Figure 12:
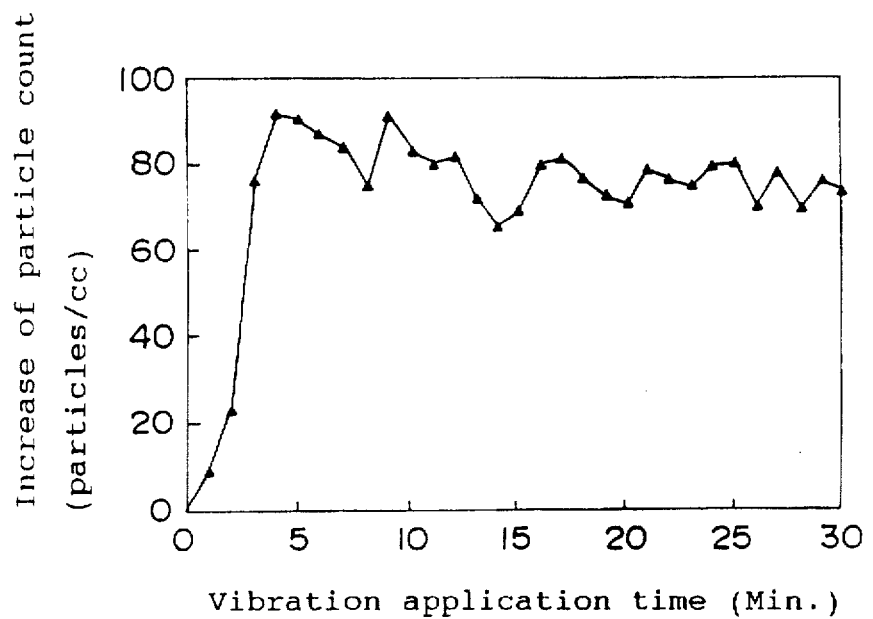
FIG. 12 is a graph showing test results in the seventh embodiment of the invention.

(3) FIG. 12 shows the result of measurement by the above method of measurement, i.e., the increase of particle count plotted against the vibration application time. As is obvious from FIG. 12, the particle count in the water 2 was substantially saturated after 10 minute of vibration application.

Test Example 8

(1) The same operation and measurement as in (1) in Test Example 7 were done.

(2) Then, sinusoidal wave low frequency vibrations at a frequency of 400 Hz and with an acceleration of 10 G from the vibrator 5, were applied to the wafer case body 1 and the water 2 therein for 10 minutes while measuring the particle count at an interval of one minute.

(3) Then, the water 2 in the wafer case body 1 was discharged, and the same amount of pure water as the discharged amount was poured again into the wafer case body 1, and after the water level stabilization the particles in the water 2 were counted with the particle measuring unit 4.

(4) Then, the same sinusoidal wave low frequency vibrations as in (2) above were applied to the wafer case body 1 and the water 2 therein for 10 minute while measuring the particle count in the water for every one minute with the particle measuring unit 4.

Figure 13:
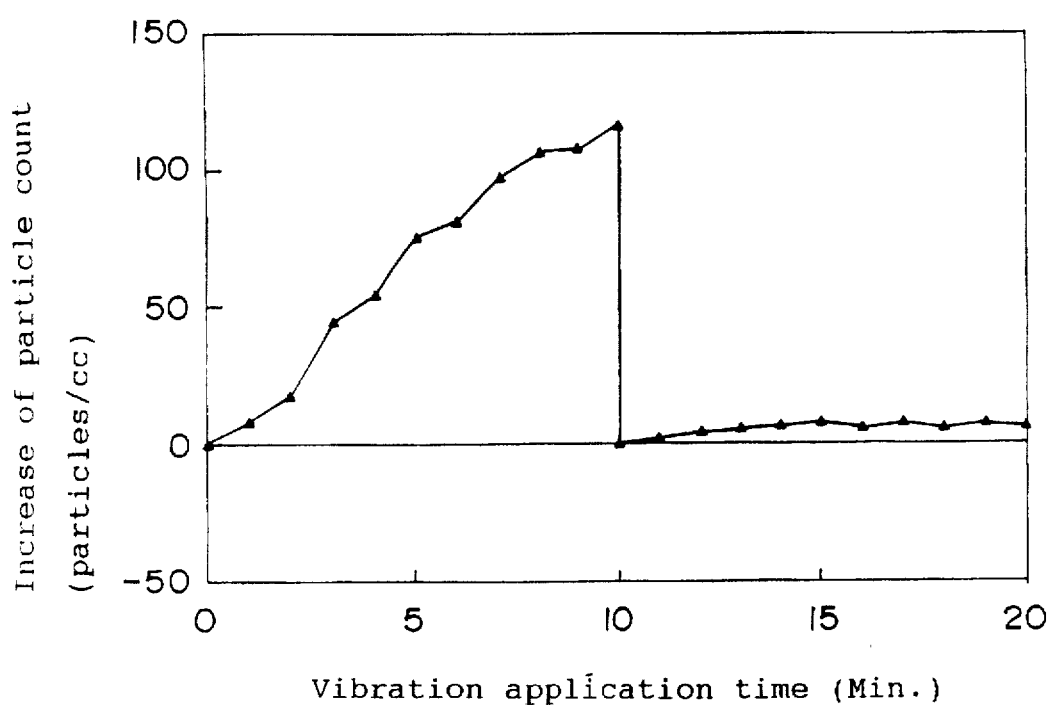
FIG. 13 is a graph showing test results in the eighth embodiment of the invention.

(5) FIG. 13 shows the result of measurement in (1) through (4) above. As is obvious form FIG. 13, after the initially poured water 2 had been discharged from the wafer case body 1, substantially no particle was detected by pouring pure water again, thus indicating that the application of the low frequency vibrations to the water 2 in the wafer case body 1 causes efficient separation of particles from the wafer case body 1.

Test Example 9

(1) Ten wafer case bodies 1 right after molding and also then ten wafer case bodies 1 having been cleaned were prepared.

(2) Pure water 2 was poured into each wafer case body 1. Then, as in Test Example 1 sinusoidal wave low frequency vibrations at a frequency of 900 Hz and with an acceleration of 20 G were applied for ten minutes, and then the particles in the water were counted.

Figure 14:
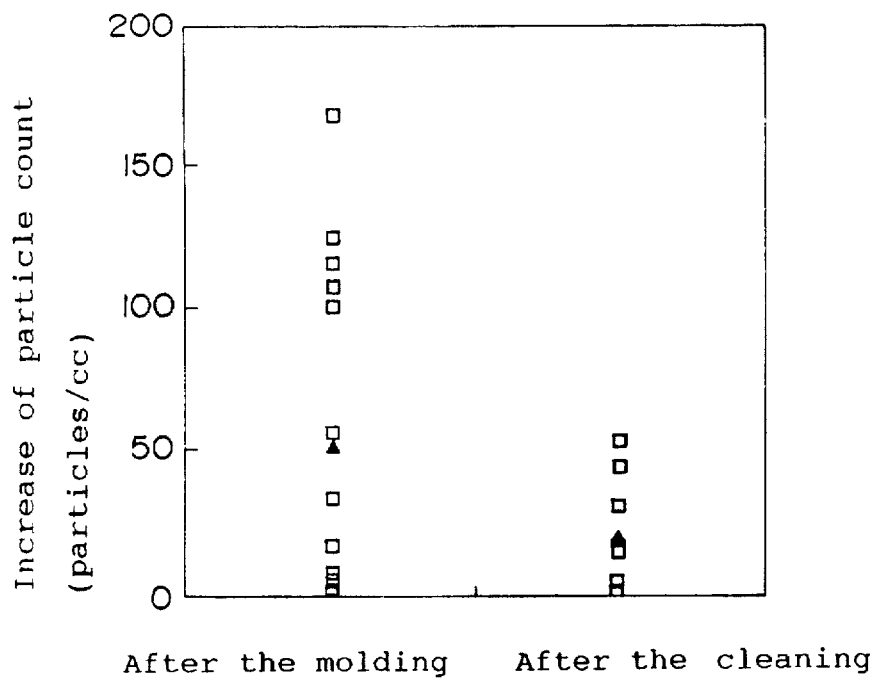
FIG. 14 is a graph showing test results in the ninth embodiment of the invention.

(3) FIG. 14 shows the result of measurement in (1) through (2) above. As is obvious from FIG. 14, the increase of particle count is far less with the wafer case bodies having been cleaned than with those right after the molding (i.e., without being washed), thus indicating increase of the cleanliness of the wafer case body by the cleaning thereof.

Test Example 10

(1) Instead of the wafer case body 1, the top cover 52 for closing the body 1 was put on the stage 6, pure water 2 was then poured into the top cover 52 in an amount corresponding to about 80% of the inner volume, and after the water level stabilization the particles having sizes of 0.2 μm and above in the water were counted.

(2) Then, sinusoidal wave low frequency vibrations at a frequency of 900 Hz and an acceleration of 30 G were applied to the top cover 52 and he water 2 therein from the vibrator 5. The vibrations were applied for 30 minutes while measuring the particle count in the water for every one minute with the particle measuring unit 4.

Figure 15:
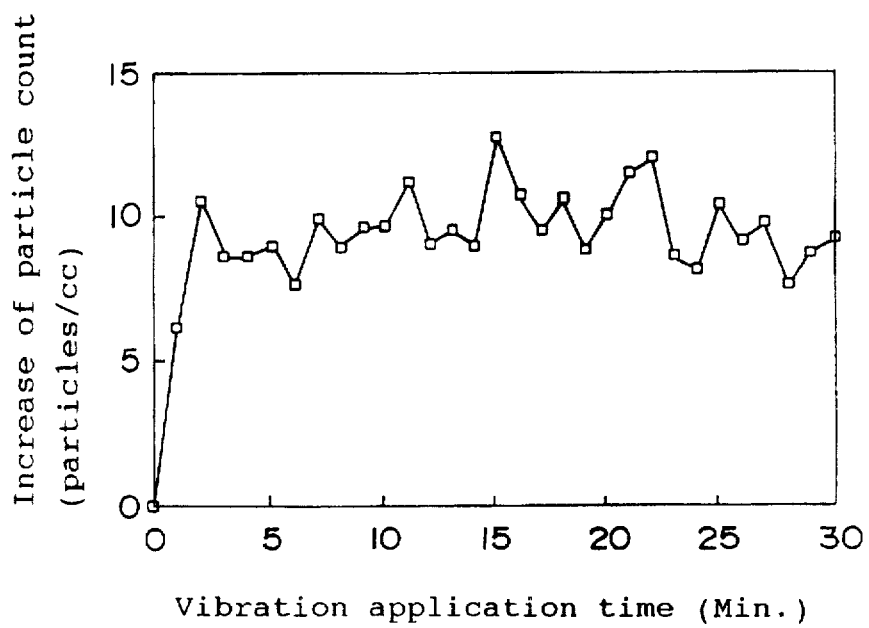
FIG. 15 is a graph showing test results in the tenth embodiment of the invention.

(3) FIG. 15 shows the result of measurement in (1) through (2) above. As is obvious from FIG. 15, the particle count in the water 2 was substantially saturated after about two minutes of vibration application.

(D) Fourth Embodiment

Figure 11:
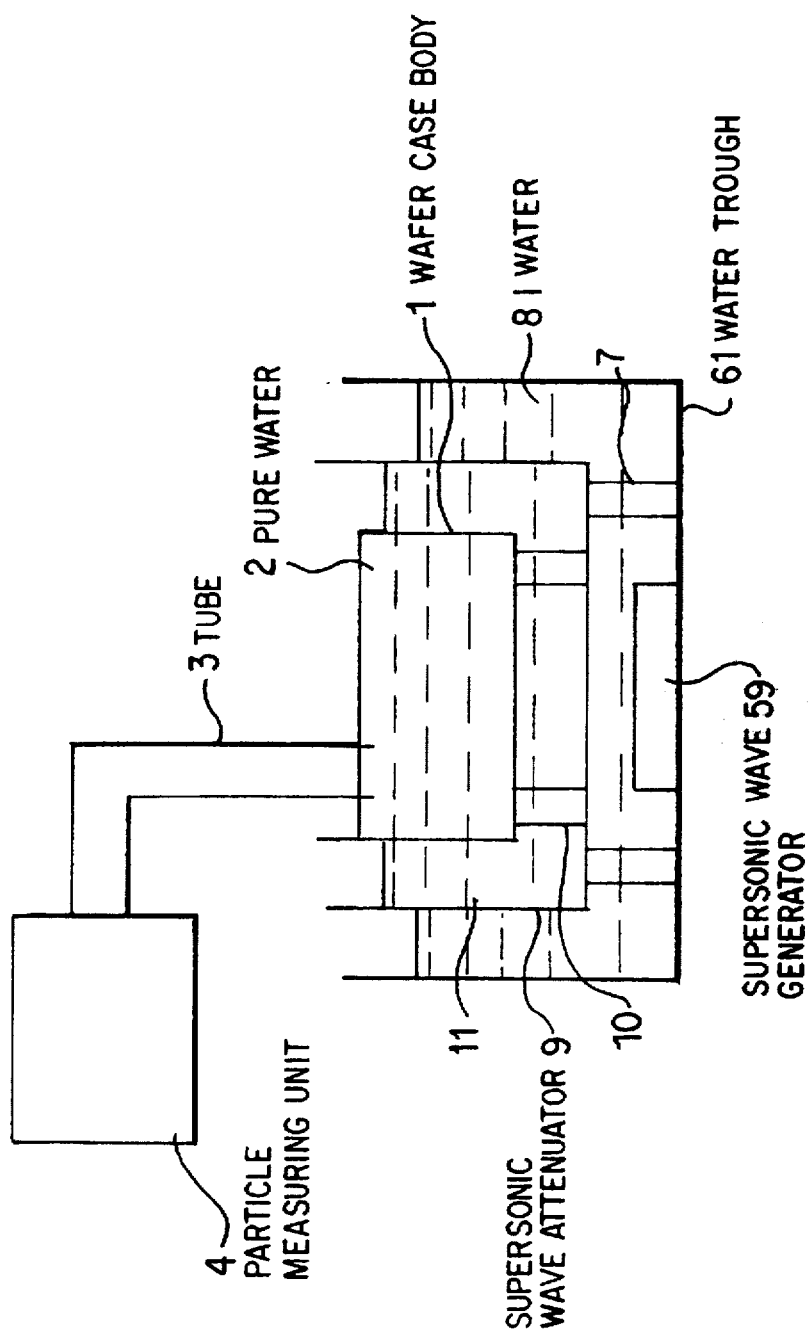
FIG. 11 is a schematic view showing an apparatus for measuring and estimating the cleanliness of a wafer case (by application of supersonic wave vibrations) according to the fourth embodiment of the invention.

FIG. 11 schematically shows an apparatus for determining wafer case cleanliness according to a fourth embodiment of the invention.

Referring to FIG. 11, reference numeral 1 designates the wafer case body shown in FIG. 3. Pure water 2 is contained in the wafer case body 1. The amount of the contained pure water 2 is adequately 35 to 95% of the inner volume of the wafer case body 1.

Reference numeral 61 designates a water trough containing water 8. A supersonic wave generator 59 is installed on the bottom of the water trough 61.

Reference numeral 9 designates a supersonic wave attenuator for attenuating the supersonic wave from the supersonic wave generator 59 down to an adequate intensity level for application to the wafer case body 1 as an under-measurement member.

The supersonic wave generator 9 is made of such material as polypropyrene, polyethylene, polycarbonate, etc.

The supersonic wave attenuator 9 is supported by a plurality of support legs 7 erected from the bottom of the water trough 61. The wafer case (under-measurement member) 1 is supported by a plurality of support legs 10 erected from the bottom of the supersonic wave attenuator 9.

A particle measuring unit 4 for measuring particles in the wafer case 1, is communicated with the water 2 in the wafer case 1 through a tube 3. The particle count in the water 2 thus can be measured progressively.

A method of measuring and estimating the cleanliness of the wafer case with the cleanliness determining apparatus shown in FIG. 11 will now be described.

Test Example 11

(1) Pure water 2 was poured into the wafer case body 1, and after the water level stabilization the particles having sizes of 0.2 μm and above were counted with the particle measuring unit 4.

(2) Then, supersonic wave vibrations at a frequency of 40 kHz and with an output of 300 W, were applied from the supersonic wave generator 5 for 20 minutes while measuring the particle count at an interval of one minute.

After the vibration application for 20 minutes, the water in the wafer case body 1 was discharged, and the same amount of pure water as the discharged amount was poured again, followed by vibration application for 10 minutes while making the particle measurement for every one minute.

Figure 16:
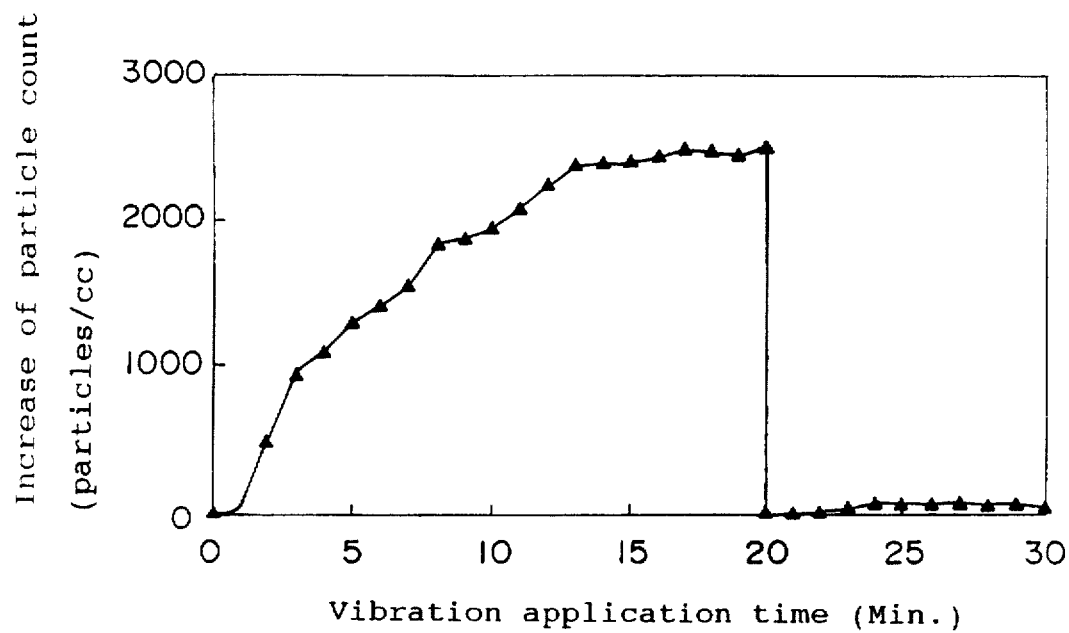
FIG. 16 is a graph showing test results in the eleventh embodiment of the invention.

(3) FIG. 16 shows the result. As is seen, the particle count in the water 2 was substantially saturated after 10 minutes of vibration application.

In addition, after the initially poured water 2 had been discharged from the wafer case body 1, substantially no particle was detected by pouring pure water again, thus indicating that the application of the supersonic wave vibrations to the water 2 in the wafer case body 1 causes efficient separation of particles from the wafer case body 1.

Test Example 12

(1) Ten wafer case bodies 1 right after molding and also ten wafer case bodies 1 having been cleaned were prepared.

(2) Pure water 2 was poured into each wafer case body 1. Then, supersonic wave vibrations at a frequency of 40 kHz and with an output of 300 W were applied from the supersonic wave generator 5 for 10 minutes, and then the particle count in the water was measured.

Figure 17:
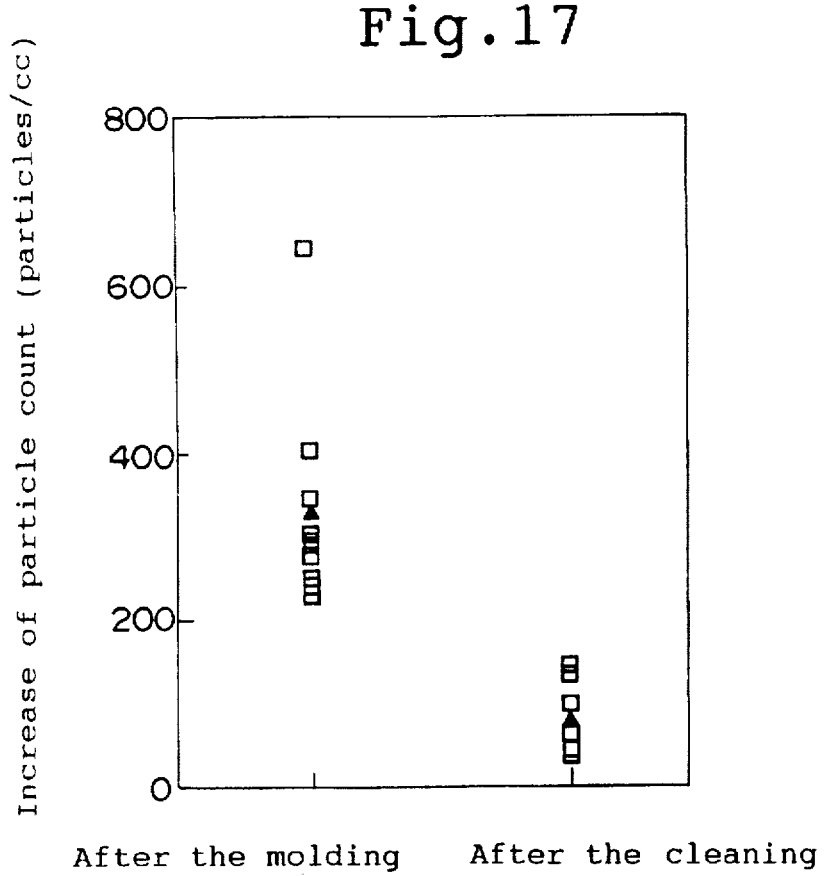
FIG. 17 is a graph showing test results in the twelfth embodiment of the invention.

(3) FIG. 17 shows the result of measurement by the above method. As is seen, the cleanliness is far better with the wafer case bodies 1 having been cleaned compared to those right after the molding (i.e., without being cleaned).

Test Example 13

(1) Instead of the wafer case body 1 the top cover 52 (see FIG. 3) was put, and pure water was poured into the top cover 52 in an amount corresponding to about 80% of the inner volume.

(2) After the water level stabilization, the particles having sizes of 0.2 μm and above in the water were counted with the particle measuring unit 4.

(3) Then, supersonic wave vibrations at a frequency of 40 kHz and with an output of 400 W were applied for 20 minutes while measuring the particle count at an interval of one minute.

After the vibration application for 20 minutes, the water in the top cover 52 was discharged, and the same amount of pure water as the discharged amount was poured again, and then the vibrations were applied for 10 minutes while making the particle count measurement for every one minute.

Figure 18:
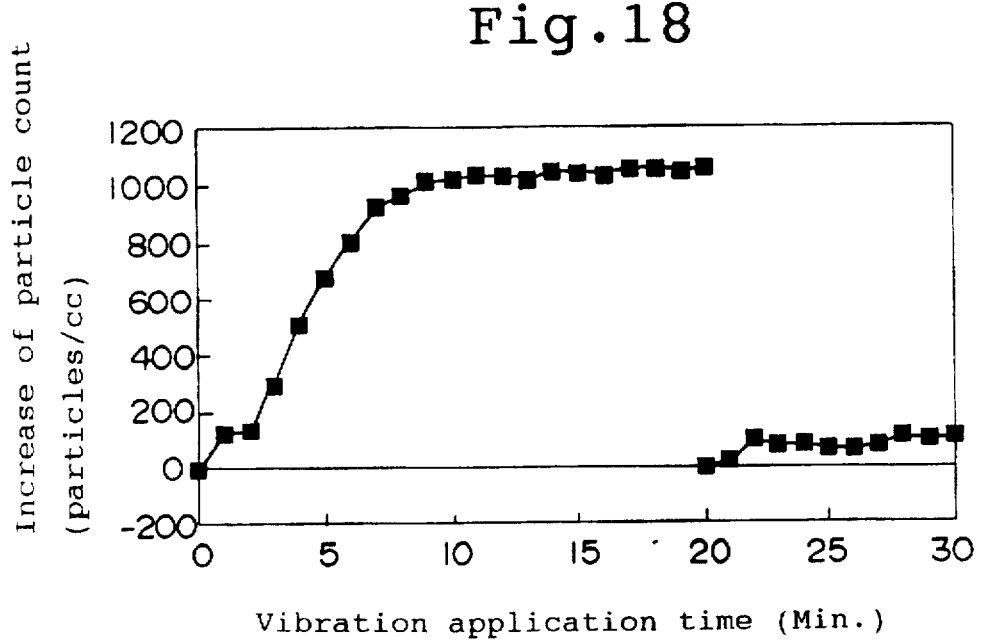
FIG. 18 is a graph showing test results in the thirteenth embodiment of the invention.

(4) FIG. 18 shows the result of measurement in (1) through (3) above. As is obvious from FIG. 18, the particle count in the water was saturated after 10 minutes.

In addition, after the initially poured water 2 had been discharged from the top cover 52, substantially no particle was detected by pouring pure water again and applying the supersonic wave vibrations, thus indicating that the application of the supersonic wave vibrations to the water 2 in the top cover 52 causes efficient separation of particles from the inner wall surfaces of the top cover 52.

As has been described in the foregoing, in the above embodiments, the low frequency vibrations or supersonic wave vibrations are applied to vessel-like wafer accommodating member capable of containing liquid, such as the wafer case body, the top cover, etc. of the wafer case, after pouring pure water into the member, or the low frequency vibrations or supersonic wave vibrations are applied to the vessel containing pure water, the wafer case accommodated in the vessel and the inner wafer accommodating members accommodated in the wafer case body, such as the wafer basket, the wafer retainer, etc., and subsequently the particle count in the water is measured. Particles that have been attached to the wafer case and the inner wafer accommodating members accommodated therein, such as the wafer basket, the wafer retainer, etc., are made readily separable into the water. It is thus possible to obtain quantitative determination of particles generated from the inner wafer accommodating members.

It is further possible to measure and estimate the cleanliness of a non-vessel-like inner wafer accommodating members, such as the wafer basket, the wafer retainer, etc., which are incapable of containing pure water and is accommodated in the wafer case, by using a vessel to accommodate these inner wafer accommodating members and pouring pure water into the vessel.

It is further possible to measure the particle count progressively by leading the water to the particle measuring apparatus, thus permitting accurate grasping of changes in the generation of particles with the lapse of time.

Particularly, application of sinusoidal wave low frequency vibrations less subject to frequency and acceleration fluctuations, permits obtaining satisfactory reproducibility of vibrations applied to the wafer case and the inner wafer accommodating member. Quantitative determination of the cleanliness of the inner wafer accommodating member is thus possible through comparison of the particle count in the water before and after the application of the low frequency vibrations for a predetermined period of time.

Likewise, application of supersonic wave vibrations less subject to frequency and output fluctuations permits obtaining satisfactory reproducibility of vibrations applied to the wafer case and the inner wafer accommodating members. Again quantitative determination of the cleanliness of the inner wafer accommodating member is thus possible through comparison of the particle count in the wafer before and after the application of the vibrations to the wafer case and the wafer accommodating member for a predetermined period of time.

According to the invention, accurate detection and determination of the cleanliness of the wafer case and the inner wafer accommodating member, are obtainable with a relative simple and low cost apparatus, in which vibrations are applied to a vessel, a wafer case accommodated therein and inner wafer accommodating members accommodated in the wafer case while measuring the particle count after pouring pure water into the vessel.

It is thus possible to determine the cleanliness of not only new wafer cases but also re-used wafer cases in the same way.

What is claimed is:

1. A method of measuring and estimating the cleanliness of wafer accommodating members used for storing or transporting semiconductor wafers comprising the steps of:

accommodating wafer accommodating members in a vessel with a bottom and then pouring a predetermined amount of pure water into the vessel, or pouring a predetermined amount of pure water directly into a wafer accommodating member in the form of a vessel with a bottom;

putting the vessel or the wafer accommodating member in the form of a vessel with a bottom after the pouring of pure water on a vibrator and counting the particles in the water after the stabilization of the water level and before the application of vibrations;

then applying low frequency vibrations to the vessel or the wafer accommodating members in the form of a vessel with a bottom from the vibrator for a predetermined period of time; and counting the particles in the water again to obtain the increase of particle count after the application of vibrations and determining the cleanliness from the increase of particle count thus obtained.

2. The method of measuring and estimating the cleanliness of wafer accommodating members according to claim 1, wherein the low frequency vibrations are sinusoidal vibrations.

3. The method of measuring and estimating the cleanliness of wafer accommodating members according to claim 1, wherein the frequency of the low frequency vibrations is set to 50 to 2,000 Hz.

4. The method of measuring and estimating the cleanliness of wafer accommodating members according to claim 1, wherein the acceleration of the low frequency vibrations is set to 2 to 50 G.

5. The method of determining the cleanliness of wafer accommodating members according to claim 1, wherein the low frequency vibrations are applied in vertical directions.

6. In a wafer case comprising a wafer basket for accommodating semiconductor wafers, a wafer retainer for the wafer basket, a wafer case body for accommodating the wafer basket and the wafer retainer, and a top cover for closing the wafer case body, the method of measuring and estimating the cleanliness of water accommodating members according to claim 1, wherein the wafer basket, wafer retainer, wafer case body and top cover accommodated in the water case, are the inner accommodating members in the vessel with a bottom, into which are poured the predetermined amount of pure water.

7. In a wafer case comprising a wafer basket for accommodating semiconductor wafers, a wafer retainer for the wafer basket, a wafer case body for accommodating the wafer basket and the wafer retainer, and a top cover for closing the wafer case body, the method of measuring and estimating the cleanliness of wafer accommodating members according to claim 1, wherein the wafer case body or the top cover is put as an under-measurement member in the form of a vessel on the vibrator after pouring pure water into the wafer case body or the top cover.

8. A method of measuring and estimating the cleanliness of wafer accommodating members used for storing or transporting semiconductor wafers comprising the steps of:

accommodating wafer accommodating members in a vessel with a bottom and then pouring a predetermined amount of pure water into the vessel, or pouring a predetermined amount of pure water directly into a wafer accommodating member in the form of a vessel with a bottom;

putting, after the pouring of pure water, the vessel with the wafer accommodating members therein or the water accommodating members in the form of a vessel with a bottom in a water trough provided with a supersonic wave generator;

counting the particles in the water after stabilization of the water level before application of a supersonic wave;

then applying supersonic wave vibrations to the vessel with the wafer accommodating members therein or the wafer accommodating member in the form of a vessel with a bottom from the supersonic ware generator for a predetermined period of time;

counting, after the supersonic wave vibration application, the particles in the water again to obtain the increase of particles count after the application of the supersonic wave; and estimating the cleanliness of the wafer accommodating member from the increase in particle count thus obtained.

9. The method of measuring and estimating the cleanliness of wafer accommodating members according to claim 8, wherein the frequency of the supersonic wave vibrations is set to 20 to 50 kHz.

10. The method of determining the cleanliness of wafer accommodating members according to claim 8, wherein the supersonic wave output is set to 300 to 400 W.

11. In a wafer case comprising a wafer basket for accommodating semiconductor wafers, a wafer retainer for the wafer basket, a wafer case body for accommodating the wafer basket and the wafer retainer, and a top cover for closing the wafer case body, the method of determining the cleanliness of wafer accommodating members according to claim 8, wherein inner wafer accommodating members accommodated in the wafer case, are accommodated in the vessel with a bottom before pouring the predetermined amount of pure water into the vessel.

12. The method of measuring and estimating the cleanliness of wafer accommodating members according to claim 11, wherein the supersonic wave vibrations are attenuated between the supersonic wave generator and the inner wafer accommodating members dipped in the water in the vessel by supersonic wave attenuating means, the attenuated supersonic wave vibrations being applied to the inner wafer accommodating members.

13. The method of measuring and estimating the cleanliness of wafer accommodating members according to claim 11, wherein the pure water is poured into the vessel unit reaching a level of 5 mm above to 40 mm below the top of the wafer accommodating members.

14. In a wafer case comprising a wafer basket for accommodating semiconductor wafers, a wafer retainer for the wafer basket, a wafer case body for accommodating the wafer basket and the wafer retainer, and a top of cover for closing the wafer case body, the method of measuring and estimating the cleanliness of wafer accommodating members according to claim 8, wherein the wafer case body or the top cover is put, after pouring pure water thereinto, as an under-measurement member in the form of a vessel in a water trough provided with a supersonic wave generator.

15. The method of measuring and estimating the cleanliness of wafer accommodating members according to claim 14, wherein the supersonic wave vibrations are attenuated between the supersonic wave generator, and the under-measurement member, by supersonic wave attenuating means, the attenuated supersonic wave being applied to the under-measurement member.

16. The method of measuring and estimating the cleanliness of wafer accommodating members according to claim 14, wherein the pure water is poured in an amount corresponding to 35 to 95% of the inner volume of the under-measurement member.

17. In a wafer case compromising a wafer basket for accommodating semiconductor wafers, a wafer retainer for the wafer basket, a wafer case body for accommodating the wafer basket and the wafer retainer, and a top cover for closing the wafer case body, an apparatus for measuring and estimating the cleanliness of inner wafer accommodating members accommodated in the wafer case, comprising:

a vessel with a bottom into which pure water is poured, the inner wafer accommodating members being dipped in the poured water;

a vibrator for vibrating the vessel; and a particle measuring apparatus coupled to the water in the vessel for measuring the particle count in the water.

18. In a wafer case comprising a wafer basket for accommodating semiconductor wafers, a wafer retainer for the wafer basket, a wafer case body for accommodating the wafer basket and the wafer retainer, and a top cover for closing the wafer case body, an apparatus for measuring and estimating the cleanliness of inner wafer accommodating members accommodated in the wafer case, comprising:

a vessel with a bottom into which pure water is poured the inner wafer accommodating members being dipped in the pure water;

a water trough for accommodating the vessel with outer wall surfaces thereof dipped in the water;

a supersonic wave generator disposed underneath the vessel in the water trough for applying supersonic wave vibrations to the inner wafer accommodating member in the vessel; and a particle measuring means coupled to the water in the vessel for measuring the particle count in the water.

19. The apparatus for measuring and estimating the cleanliness of the wafer accommodating member according to claim 18, wherein a supersonic wave attenuating means for attenuating the supersonic wave is provided between the supersonic wave generating means and the vessel.

20. The apparatus for measuring and estimating the cleanliness of the water accommodating member according to claim 19, wherein the supersonic wave attenuating means is in the form of a vessel with a bottom, the inner wafer accommodating members being accommodated in the vessel, and is made of polypropyrene, polyethylene or polycarbonate.

21. An apparatus for measuring and estimating the cleanliness of a wafer accommodating members including a wafer basket body for accommodating a wafer basket for accommodating semiconductor wafers and a top cover for the wafer case body, the apparatus comprising:

a vibrator for vibrating the wafer case body or the top cover as an under-measurement member in the form of a vessel under a condition that the under-measurement member contains a predetermined amount of poured pure water; and a particle measuring apparatus coupled to the water in the under-measurement member for measuring the particle count in the water.

22. An apparatus for measuring and estimating the cleanliness of a wafer accommodating members including a wafer basket body for accommodating a wafer basket for accommodating semiconductor wafers and a top cover for the wafer case body, the apparatus comprising:

- an under-measurement member in the form of a vessel constituted by the wafer case body or the top cover and containing poured pure water;
- a water trough accommodating the under-measurement member such that outer wall surfaces thereof are dipped in the water;
- a supersonic wave generator disposed underneath the under-measurement member in the water trough for applying a supersonic wave to the under-measurement member; and
- a particle measuring unit coupled to the water in the under-measurement member for measuring the particle count in the water.

23. The apparatus for measuring and estimating the cleanliness of a wafer accommodating member according to claim 22, wherein a supersonic wave attenuating means for attenuating the supersonic wave is provided between the supersonic wave generator and the under-measurement member.

24. The apparatus for measuring and estimating the cleanliness of a wafer accommodating member according to claim 22, wherein the wafer case body for accommodating the wafer basket for accommodating semiconductor wafer and the top cover are under-measurement members, and the supersonic wave attenuating means is in the form of a vessel capable of accommodating the under-measurement members and made of polypropyrene, polyethylene or polycarbonate.

* * * * *